United States Patent [19]

Schellenbaum

[11] 3,956,402
[45] May 11, 1976

[54] SUBSTITUTED BIS-HYDROXYPHENYL PENTANES

[75] Inventor: Max Schellenbaum, Muttenz, Switzerland

[73] Assignee: Ciba-Geigy Corporation, Ardsley, N.Y.

[22] Filed: Feb. 12, 1975

[21] Appl. No.: 549,254

Related U.S. Application Data

[63] Continuation of Ser. No. 390,477, Aug. 22, 1973, abandoned.

[30] Foreign Application Priority Data

Aug. 29, 1972 Switzerland............... 12754/72

[52] U.S. Cl. .................. 260/619 B; 71/122; 252/106; 252/107; 260/566 B; 260/591; 424/347
[51] Int. Cl.² ........................ C07C 39/16
[58] Field of Search .................. 260/619 B

[56] References Cited
UNITED STATES PATENTS

| | | | |
|---|---|---|---|
| 3,471,576 | 10/1969 | Klespar et al. ................ | 260/619 B |
| 3,499,763 | 3/1970 | Clecuk et al. ................ | 260/619 B |

OTHER PUBLICATIONS

Richardson et al., "J.A.C.S.," Vol. 62, pp. 413–415, (1940).

Kakemi et al., "C.A.," Vol. 65, 20042g–20043a, (1966).

*Primary Examiner*—Norman Morgenstern
*Attorney, Agent, or Firm*—Joseph G. Kolodny; Edward McC. Roberts; Prabodh I. Almaula

[57] ABSTRACT

The present invention relates to new bis-hydroxyphenyl-alkanes of the formula I

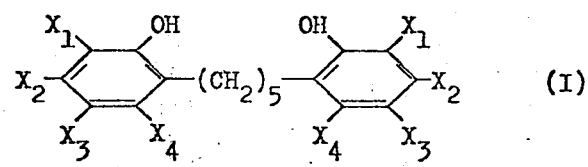

(I)

wherein one of the radicals $X_1$ to $X_4$ represents halogen and the others represent hydrogen, halogen, or alkyl, process for their manufacture, agents which contain these new compounds, and to the use of the new compounds for combating microorganisms and for material protection.

3 Claims, No Drawings

SUBSTITUTED BIS-HYDROXYPHENYL PENTANES

This is a continuation of application Ser. No. 390,477 filed on Aug. 22, 1973, now abandoned.

The present invention relates to new bis-hydroxyphenyl-alkanes, process for their manufacture, agents which contain these new compounds, and to the use of the new compounds for combating microorganisms and for material protection.

Bis-hydroxyphenyl-alkanes are already known. A group of hitherto unknown compounds with surprising properties has now been discovered.

These new bis-hydroxyphenyl-alkanes correspond to the formula I

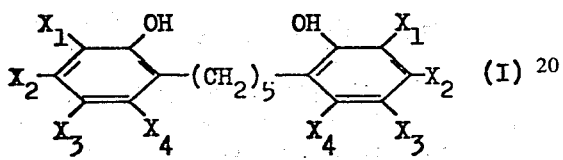

wherein one of the radicals $X_1$ to $X_4$ represents halogen and the others represent hydrogen, halogen, or alkyl.

Of primary interest for the objectives and functions according to the invention are compounds of the formula I in which one of the radicals $X_3$ or $X_4$ represents halogen, preferably chlorine or bromine, and the other represents hydrogen, and $X_1$ and $X_2$ represent halogen, preferably chlorine or bromine, or alkyl, preferably with 1 to 4 carbon atoms.

Particularly preferred compounds of this group are those of the formula I in which $X_1$ and one of the radicals $X_2$, $X_3$ and $X_4$ represent hydrogen, one of the radicals $X_2$, $X_3$ and $X_4$ represent chlorine or bromine, and the remaining raidcal $X_2$, $X_3$ or $X_4$ represent hydrogen, chlorine, bromine or methyl.

Suitable alkyl radicals within the scope of the invention are both straight-chain and branched radicals, e.g. methyl, ethyl, n-propyl, isopropyl, n-butyl, sec.butyl and tert. butyl.

Particularly interest attaches to bis-hydroxyphenyl-alkanes of the following formulae II to VII

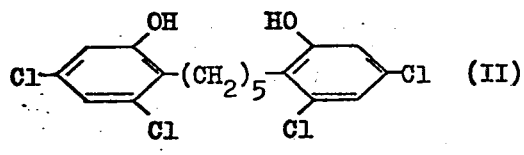

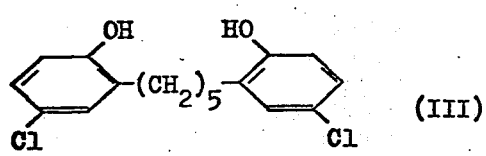

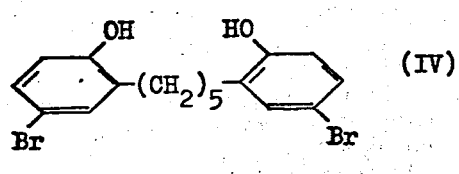

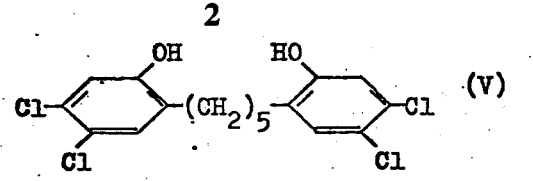

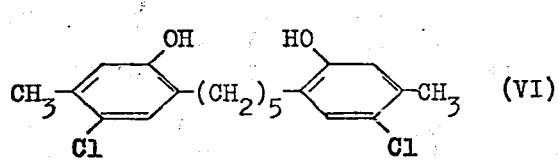

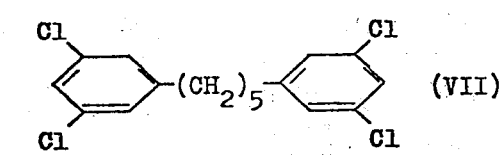

The invention is based on the surprising observation that, on account of their special substitution, the novel compounds of the formula I proposed according to the invention are also highly active against gram-negative bacteria and against mold fungi. Advantageously, the compounds exhibit a markedly broad activity spectrum, but only low toxicity. They can also be used with success as nutritional supplements in animal feeds for promoting the growth of productive livestock. A particular advantage of the compounds according to the invention is to be observed in the fact that, even in relatively low concentrations, their activity extends beyond a simple inhibitory effect to a total destruction of the microorganisms to be combated. With regard to the technical aspects of their use, the colourlessness of the compounds according to the invention and their insignificant emission of odour are of especial value.

The bis-hydroxyphenyl-alkanes according to the invention can be manufactured by reduction of ketones of the formula VIII

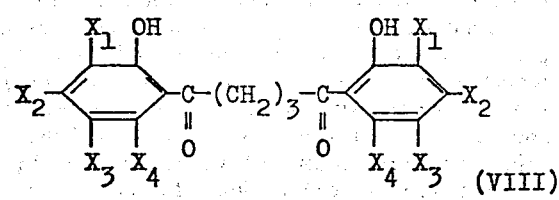

wherein $X_1$ to $X_4$ have the meanings given hereinbefore. Accordingly, it is possible to manufacture e.g. the compounds of the formulae II, III, IV, V, VI, and VII from the ketones of the formulae IX, X, XI, XII, XIII, and XIV:

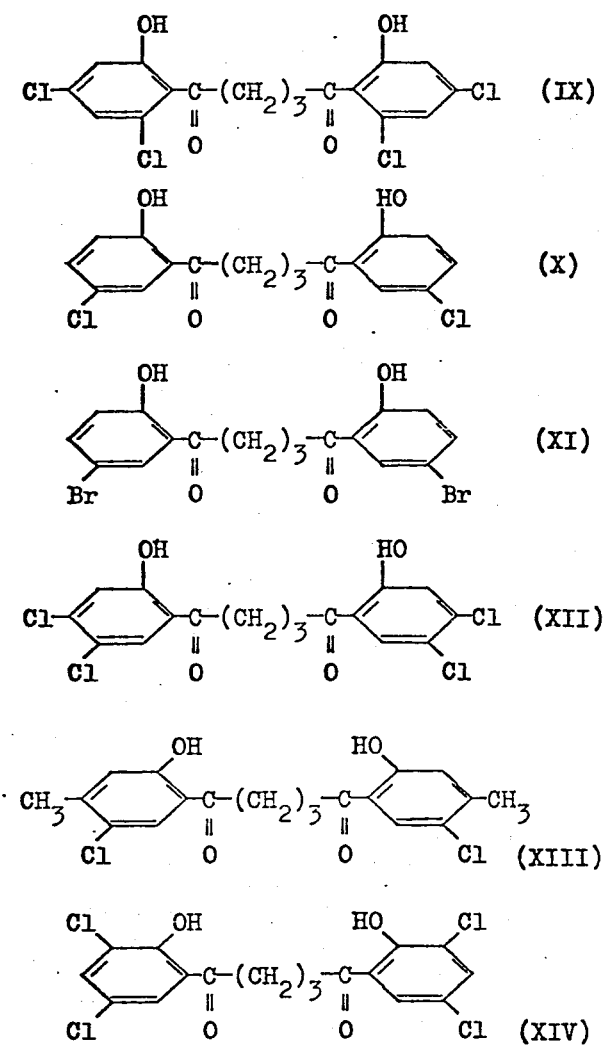

The reduction of the ketones can be carried out by various methods which are known in the art. Thus it is possible, for example, to use successfully the reduction method of Wolff-Kisher (cf. D. Todd, Organic Reactions 4, 378; 1948). This consists in converting the particular ketone firstly into the hydrazone and reducing this latter with sodium methylate at elevated temperature and under pressure to the corresponding hydrocarbon. According to a modified process of Huang-Minlon, Journal of the American Chemical Society 68, 2487; 1946) the decomposition of the hydrazone takes place in an inert solvent at elevated temperature - but at normal pressure - using an inorganic base. Advantageously the procedure to be followed is that the ketone is heated firstly in an inert, high-boiling, water-miscible solvent together with an excess of hydrazine hydrate and an alkali hydroxide to 100°–150°C, and then the resulting hydrazone, after the water and excess hydrazine hydrate have been distilled off, is decomposed by heating it to 180°–220°C.

Particularly good yields are obtained by using a glycol, e.g. ethylene glycol, diethylene glycol, or triethylene glycol, as solvent. It is advantageous to use sodium or potassium hydroxide as alkali hydroxide, as a rule in an amount of 6 to 14 moles per mole of ketone. The formation of the hydrazone succeeds best if the process is carried out at a temperature of 120°–140°C with excess of 6 to 14 moles of hydrazine hydrate per mole of ketone. The resulting hydrazone is decomposed most advantageously at a temperature between 190°–210°C. The reaction times required for the formation of the hydrazone are between 30 minutes and 3 hours, and those for decomposition of the hydrazone between 1 and 5 hours.

The Clemmensen reduction (cf. E. Clemmensen, Berichte der deutschen Chemischen Gesellschaft 46, 1837; (1913) and 47, 51,681; (1914), also E. L. Martin Journal of the American Society 58, 1438; (1936) is a further good method for manufacturing the bis-hydroxyphenyl-alkanes according to the invention from the corresponding ketones. Here the reduction is carried out by heating the ketones with amalgamated zinc and hydrochloric acid, optionally in the presence of an organic solvent. Owing to the poor water-solubility of the ketones of the formulae VIII, it is advantageous to carry out the reduction in the presence of water-miscible organic solvents, e.g. ethanol, acetic acid, or dioxan. The reduction gives particularly good yields if 15 to 30 gram atoms of zinc amalgam are used per mole of ketone.

The reaction temperature can vary between e.g. 20°C and the boiling temperature of the solvent used. The reaction times are accordingly from 48 hours to 1 hour.

A further possible reduction method is the splitting by hydrogenation of the dialkylthioketals or ethylenethioketals manufactured from the ketones of the formula VIII with Raney nickel (cf. L. F. Fieser and W. Y. Huang, Journal of the American Chemical Society 75, 5356; (1953).

Attention may also be drawn to the catalytic hydrogenation of the ketones of the formula VIII to the compounds of the formula I according to the invention.

The ketones of the formula VIII used as starting products are known (cf. N. F. Hayes and R. H. Thomson, Journal of the American Society London 1956, 1585) or they are manufactured by methods known in the art, for example from the corresponding alkanedicarboxylic acid phenyl esters by the Fries reaction (cf. Baltzly et al., Journal of the American Chemical Society 77, 2522; (1955) or G. A. Olah, Friedel-Crafts and Related Reactions 1964, page 499). This reaction can be carried out in the melt or in the presence of an organic solvent, e.g. nitrobenzene. The ketones of the formula VIII are then formed by heating the corresponding phenyl ester together with aluminium chloride.

As a further method of manufacturing the compounds of the formula I according to the invention mention may be made of the chlorination or bromination of compounds of the formula XV

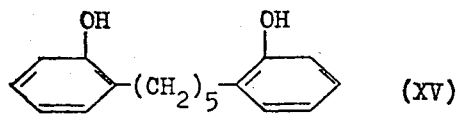

The compounds of the formula I exhibit good solubility in organic solvents. Their water-soluble salts, in particular the alkali and alkaline earth salts, are also effective and of especial significance whenever an application in aqueous medium and soaps is contemplated.

The antimicrobial compounds of the present invention can be used on a very broad basis, in particular for protecting organic substrates against attack by harmful and pathogenic microorganisms. The antimicrobial agents are suitable accordingly as preservatives and disinfectants for industrial products of all kinds.

As examples of industrial products which can be preserved with the compounds of the formula I according to the invention the following may be mentioned: adhesive substances, binding agents, paints, textile auxiliaries and finishing agents, oil pastes and printing pastes and similar preparations based on organic and inorganic dyestuffs and pigments, also those which contain casein or other organic compounds as admixtures. Also wall and ceiling paints, for example those which contain an albuminous colour binder, are protected against attack by pests by addition of the compounds according to the invention. Their use for protecting wood is also possible.

The compounds according to the invention can also be used as preservatives in the pulp and paper industry, inter alia for preventing the known formation of mucilage caused by microorganisms in the apparatus used for manufacturing paper.

The action of the compounds according to the invention can also be utilised in providing plastics with preservative and disinfectant finishes. In the use of plasticisers it is advantageous to add the antimicrobial agent to the plastic in the plasticiser in dissolved or dispersed form. It is expedient to ensure as uniform a distribution in the plastic as possible. The plastics with antimicrobial properties can be used for commodities of all kinds in which an activity against bacilli of the most diverse kinds, for example bacteria and fungi, is desired, thus for example for foot mats, bathroom curtains, seating accomodation, steps in swimming baths, wall hangings etc. By incorporating the compounds according to the invention into corresponding wax compositions and floor polishing pastes there are obtained floor and furniture polishes with disinfectant action.

The compounds according to the invention are used with advantage for providing fibres and textiles with a preservative and disinfectant finish. They can be applied to natural and synthetic fibres on which they exert a lasting action against harmful (also pathogenic) microorganisms, for example fungi and bacteria. The compounds can be added before, simultaneously with, or after a treatment of these textiles with other substances, e.g. oil or printing pastes, flameproofing agents, agents for producing a soft handle, and other finishing agents. Textiles thus treated also have protection against perspiration odour caused by microorganisms.

The forms in which the active substances according to the invention are applied correspond to the usual formulations. The agents used for the finishing or for the protection of textiles should contain the active substances in a finely divided form: in particular, solutions, dispersions and emulsions of the active substances therefore find application. Aqueous dispersions can be obtained, for example, from pastes or concentrates, and can be applied as liquids or in the aerosol form.

The aqueous solutions or dispersions advantageously contain surface-active agents; for example, anionic compounds such as soaps and other carboxylates (e.g. alkali salts of higher fatty acids), derivatives of sulphuroxyacids (e.g. sodium salt of dodecylbenzenesulphonic acid, water-soluble salts of sulphuric acid monoesters of higher molecular alcohols or of their polyglycol ethers, for example soluble salts of dodecyl alcohol sulphate or of dodecyl alcohol polyglycol ether sulphate), derivatives of phosphorusoxyacids (e.g. phosphates), derivatives with acid (electrophilic) nitrogen in the hydrophilic group (e.g. disulphine salts), cationic surface-active agents, such as amines and their salts (e.g. lauryldiethylenetriamine), onium compounds, amine oxides or nonionic surface active agents, e.g. polyhydroxy compounds, surface-active agents based on mono- or polysaccharide, higher molecular acetylene glycols, polyglycol ethers (e.g. polyglycol ethers of higher fatty alcohols, polyglycol ethers of higher molecular-alkylated phenols). In addition, the liquor can contain conventional adjuvants, for example water-soluble perborates, polyphosphates, carbonates, silicates, optical brighteners, plasticisers, acid reacting salts, e.g. ammonium- or zincsilicofluoride, or certain organic acids, e.g. oxalic acid, also finishing agents, e.g. those based on synthetic resin or on starch.

The textile materials can be impregnated with the active substances, e.g., by means of hot or cold aqueous dyeing, bleaching, chroming or aftertreatment baths, whereby various textile-finishing processes are suitable, e.g. the padding or exhaustion process.

On account of their better solubility in organic solvents, the active substances are also suitable for application from non-aqueous media. The materials to be finished or preserved can in this case be simply impregnated with the solutions.

Suitable organic solvents are, for example, trichloroethylene, methylene chloride, hydrocarbons, propylene glycol, methoxyethanol, ethoxyethanol or dimethylformamide, to which may also be added dispersing agents (e.g. emulsifiers, such as sulphated castor oil, fatty alcohol sulphates, etc.), and/or other auxiliaries.

Depending on the purpose of application, the content of active substances according to the present invention can be between 0.1 and 50 g, preferably between 1 and 30 g, of active substance per liter of treatment liquid.

The active substances according to the present invention can be used on their own, or together with other known antimicrobial textile-preserving agents.

Suitable as textiles to be finished or preserved are both fibres of natural origin, such as cellulose-containing fibres, e.g. cotton, or polypeptide-containing fibres, e.g. wool or silk, and fibre materials of synthetic origin, such as those based on polyamide, polyacrylonitrile or polyester, as well as blends of these fibres.

In most cases, the textile materials are adequately preserved against infestation by fungi and bacteria by a content of 0.01 to 5%, preferably 0.1 to 3%, of active substance, based on the weight of the textile materials.

Detergents and cleansing agents having excellent antibacterial or antimycotic action are obtained by combining the compounds according to the invention with interfacial-active substances, especially with active detergents.

The detergents and cleansing agents can be in any desired form, e.g. in liquid, pasty, solid, flake or granular form. The compounds according to the invention can be incorporated into anionic compounds, such as soaps and other carboxylates (e.g. alkali salts of higher fatty acids), derivatives of sulphur-oxyacids (e.g. sodium salt of dodecylbenzenesulphonic acid, water-soluble salts of sulphuric acid monoesters of higher-molecular alcohols or of their polyglycol ethers, for example soluble salts of dodecyl alcohol sulphate or of dodecyl alcohol polyglycol ether sulphate), derivatives of phosphorusoxyacids (e.g. phosphates), derivatives with acid (electrophilic) nitrogen in the hydrophilic group (e.g. disulphine salts), as well as into cationic surface active agents, such as amines and their salts (e.g. lauryldiethylenetriamine), onium compounds, amine oxides or nonionic surface-active agents, such as polyhydroxy compounds, surface-active agents based on mono- or polysaccharide, higher-molecular acetylene glycols, polyglycol ethers (e.g. polyglycol ethers of higher fatty alcohols, polyglycol ethers of higher-molecular alkylated phenols), or into mixtures of different surfactants. The antimicrobial activity of the new compounds is therewith completely retained. The active substance content of the detergents and cleansing agents, based on the weight of this agent, is generally from 0.01 to 5%, mostly 0.1 to 3%. Aqueous preparations of such detergents and cleansing agents containing compounds according to the invention can be employed, for example, for the antimicrobial finishing of textile materials, since the active substance eau be absorbed substantively on to the textile material. They are also suitable as antimicrobial cleansing agents in the food manufacturing and bottling industries, e.g. in breweries, dairies, cheese dairies and slaughterhouses.

Furthermore, the compounds according to the invention can also be used in cosmetic preparations e.g. volatile oils, bath salts, brilliantines, ointments, face lotions, hair-dyeing preparations, hair oils, hair tonics, skin creams, skin oils, Eau-de-Cologne, perfumes, powders, rouge, depilatories, sun-ray filter creams, dental hygiene products, etc., in consequence of which there is additionally imparted to these products an antimicrobial action. In general, an active-substance content, based on the total weight of the product, of 0.01 to 5%, preferably of 0.1 to 3%, suffices.

For the purpose of disinfection and preservation, the compounds of formula I can also be used in combination with known antimicrobial agents. These include, e.g.:

Halogens and halogen compounds with active halogen e.g. sodium hypochlorite, calcium hypochlorite, chloride of lime, sodium-p-toluenesulphochloramide, p-toluenesulphodichloramide, N-chlorosuccinimide, 1,3dichloro-5, 5-dimethyl-hydantoin, trichloroisocyanuric acid, potassiumdichloroisocyanurate, iodine, iodine trichloride, complex compounds of iodine and iodine trichloride with surfaceactive agents such as polyvinylpyrrolidone, alkylphenoxypolyglycols, polyoxypropylene glycols, alkylaminoethanesulphonic acids and -sulphonates, alkylarylsulphonates, quaternary ammonium compounds.

Boron compounds e.g. boric acid, borax.

Organometallic compounds e.g. bis-tributyltin oxide, triphenyltin hydroxide, tributyltin salicylate, tributyltin chloride, phenylmercury borate, phenylmercury acetate.

Alcohols e.g. hexyl alcohol, trichloroisobutyl alcohol, 1,2-propylene glycol, triethylene glycol, benzyl alcohol, 4-chlorobenzyl alcohol, 2,4- and 3,4-dichlorobenzyl alcohol, 2-phenylethyl alcohol, 2-(4-chlorophenyl)-ethyl alcohol, ethylene glycol monophenyl ether, menthol, linalool and 2-bromo-2-nitropropanediol-1,3.

Aldehydes e.g. formaldehyde, paraformaldehyde, glutaraldehyde, benzaldehyde, 4-chlorobenzaldehyde, 2,4- and 3,4-dichlorobenzaldehyde, cinnamaldehyde, salicyclic aldehyde, 3,5-dibromosalicylic aldehyde, 4-hydroxybenzaldehyde, anisaldehyde and vanillin.

Carboxylic acids and derivatives e.g. trichloroacetic acid, monobromoacetic acid glycol ester, Na- and Ca-propionate, caprylic acid, undecylenic acid, Zn-undecylenate, sorbic acid, K- and Ca-sorbate, lactic acid, malonic acid, aconitic acid, citric acid, benzoic acid, 4-chlorobenzoic acid, benzoic acid benzyl ester, salicylic acid, 4-chlorosalicylic acid-n-butylamide, salicylanilide, 3,4', 5-tribromosalicylanilide, 3,3',4'5-tetrachlorosalicylanilide, 4-hydroxybenzoic acid, 4-hydroxybenzoic acid ethyl ester, gallic acid, mandelic acid, phenylpropionic acid, phenoxyacetic acid, dehydracetic acid and vanillic acid propyl ester.

Phenols e.g. phenol, mono- and polychlorophenols, cresols, 4- chloro-3-methylphenol, 4-chloro-3,5-dimethylphenol, thymol, 4-chlorothymol, 4-t-amylphenol, saligenin, 4-n-hexylresorcin, carvacrol, 2-phenylphenol, 2-benzyl-4-chlorophenyl, 2,2'-dihydroxy-5,5'-dichlorodiphenylmethane, 2,2'-dihydroxy-3,3',5,5',6,6'-hexachloro-diphenylmethane, 2,2'-dihydroxy-5,5'dichloro-diphenylsulphide, 2,2'-dihydroxy-3,3',5,5'-tetrachlorodiphenylsulphide, 2-hydroxy-2',4,4'-trichlorodiphenyl ether and dibromosalicyl.

Quinones e.g. 2,5-dimethylquinone, 2,3,5,6-tetrachloro-benzoquinone, 1,4-2,3-dichloro-1,4-naphthoquinone.

Carbonic acid derivatives e.g. pyrocarbonic acid diethyl ester, tetramethylthiuram disulphide, 3,4,4'-trichloro-N,N'-diphenylurea, 3-trifluoromethyl-4,4'-dichloro-N.N'-diphenylurea, N-3-trifluoromethylphenyl-N'-2-ethylhexyl-urea, 1,6-bis-(4'-chlorophenyl-diguanidino)-hexane, dodecylmethylguanidine acetate, ammonium rhodanide, 4,4'-diamino-$\alpha\omega$-diphenoxyhexane.

Amines e.g. dodecylpropylenediamine, dodecyldiethylenetriamine and diaminobenzene-dihydroiodide.

Quaternary ammonium compounds e.g. alkyl-dimethyl-benzyl-ammonium chloride, alkyl-dimethyl-ethyl-benzyl-ammonium chloride, dodecyl-dimethyl-3,4-dichlorobenzyl-ammonium chloride, dodecyl-di-(2-hydroxyethyl)-benzyl-ammonium chloride, dodecyl-di-(2-hydroxyethyl) -benzyl-ammonium-pentachlorophenolate, dodecyl-di-(2-hydroxyethyl)-benzyl-ammonium-4-methyl benzoate, dodecyl-dimethyl-phenoxyethyl-ammonium bromide, 4-diisobutyl-phenoxyethoxyethyl-dimethyl-benzyl-ammonium chloride, 4-diisobutyl-cresoxyethoxyethyl-dimethyl-benzyl ammonium chloride, dimethyl-didecyl-ammonium chloride, cetyl trimethylammonium bromide, dodecyl-pyridinium chloride, cetyl-pyridinium chloride, dodecyl-isoquinolinium chloride, decamethylene-bis-4-aminoquinaldinium dichloride, $\alpha$-(p-tolyl)-dodecyl-trimethyl-ammonium methosulphate, (dodecanoyl-N-methyl-aminoethyl)-phenylcarbamoyl-methyl)-dimethylammonium chloride.

Quaternary phosphonium compounds e.g. dodecyl-triphenyl-phosphonium bromide.

Amphoteric compounds e.g. dodecyl-di-(aminoethyl)-glycine.

Heterocyclic compounds e.g. 2-mercaptopyridine-N-oxide, Na- and Zn-salt of 2-mercaptopyridine-N-oxide, 2,2'-dithiopyridine-1,1'-di-N-oxide, 8-hydroxyquinoline, 5-chloro-8-hydroxyquinoline, 5-chloro-7-iodine-8-hydroxyquinoline, 5,7-dichloro-8-hydroxyquinoline, 5,7-dichloro-8-hydroxyquinaldine, bis-2-methyl-4-amino-quinolyl-carbamide-hydrochloride, 2-mercaptobenzthiazole, 2-(2'-hydroxy-3',5'-dichlorophenyl)-5-chlorobenzimidazole, 2-aminoacridine-hydrochloride, 5,6-dichlorobenzoxazolone, 1dodecyl-2-iminoimidazolinehydrochloride and 6-chloro-benzisothiazolone.

The applicability of compounds of formula I for combating microorganisms, particularly bacteria and fungi, and for preserving organic materials and objects against infestation by microorganisms, is very extensive. Thus, for example, they can be incorporated direct into the material to be preserved, e.g. into material having a synthetic resin base, such as polyamides and polyvinyl chloride, into paper-treatment liquors, into printing thickeners made from starch or cellulose derivatives, into lacquers and paints which contain, for example, casein, into cellulose, viscous spinning solutions, paper, into animal mucus or oils, into permanent coatings based on polyvinyl alcohol, cosmetic articles, and into ointments or powders. They can also be added to preparations of inorganic or organic pigments for the paint industry, to plasticisers, etc..

The compounds of formula I can be used furthermore in the form of their organic solutions, e.g. as sprays, or as dry-cleaning agents, or for the impregnation of wood, suitable organic solvents being preferably solvents immiscible with water, particularly petroleum fractions, but also solvents miscible with water, such as lower alcohols, e.g. methanol or ethanol or ethylene glycol monomethyl ether, or -monoethyl ether. Some of the new compounds can be used also in aqueous solution.

Furthermore, they can be used together with wetting or dispersing agents, in the form of their aqueous dispersions, e.g. for the preservation of substances which tend to rot, for example for the preservation of leather, paper etc..

Solutions or dispersions of active substances, which can be employed for the preservation of these materials, preferably have an active-substance content of at least 0.005 g/liter, e.g. 0.01 to 5, preferably 0.1 to 3 g/liter.

The compounds of the present invention also have an excellent growth-promoting action in production livestock, e.g. pigs and poultry, as well as ruminants, such as cattle or sheep.

The active substances can be administered to the animals perorally or via the abomasum, or by means of injection, in the form of solutions emulsions, suspensions, powders, tablets, boluses and capsules, either as a single dose or as repeated doses. The active substances or mixtures containing them may also be added to the feed or to the drinking trough, or can be contained in so-called pre-mixes.

By virtue of their wide microbiocidal activity spectrum, the compounds of the present invention can also be used in veterinary medicine for the control of pathogenic microorganisms on and in animals, particularly on the skin and in the intestinal tract and urogenital system. For the control of pathogenic microorganisms in veterinary medicine and/or the attainment of a growth-promoting action in productive livestock, the compounds of the present invention can be combined with the following substances.

1. Antibiotics:
Penicillin and its derivatives,
Cephalosporin and its derivatives,
Chloramphenicol,
Tetracyclines (e.g. chlorotetracycline, oxytetracycline),
Rifamycin and its derivatives (e.g. Rifampin)
Lincomycin
Bacitracin and its salts,
Pyrrolnitrin,
Myxin,
Streptomycin,
Nigericin,
Parvulin,
Spiramycin,
Neomycin,
Thiopeptin,
Tylosin.

2. Sulphonamides:
N'-(3,4-dimethyl-5-isoxazolyl)-sulphanilamide,
N'-2-pyrazinylsulphanilamide,
2,4-dimethoxy-6-sulphamylamino-1,3-diazine,
N'-(4-methyl-2-pyrimidyl)-sulphanilamide.

3. Nitrofurans:
3-(5-nitrofurfurylideneamino)-2-oxazolidinone,
5-morpholinomethyl-3-(5-nitrofurfurylideneamino)-2- oxazolidinone,
3-amino-6-[2-(nitro-2-furyl)vinyl]-pyridazine,
1,5-di-(5'-nitro-2'-furyl)-penty-1,4-dien-one-(3)-2'''-amidino hydrazone-hydrochloride.

4. Diaminopyrimidines:
2,4-diamino-5-(3,4,5trimethoxybenzyl)-pyrimidine,
2,4-diamino-5-(3,4-dimethoxybenzyl)-pyrimidine,
2,4-diamino-5-(p-chlorophenyl)-6-ethylpyrimidine.

5. Hydroxyquinolines:
5,7-dichloro-8-hydroxyquinaldine,
5-chloro-7-iodo-8-hydroxyquinoline.

6. Hydroxyquinolinecarboxylic acids and hydroxynaphthyridine acids;
1-ethyl-1,4-dihydro-7-methyl-4-oxo-1,8-napthyridine-3-carboxylic acid,
oxolinic acid.

7. Quinoxaline-di-N-oxides:
quinoxaline-1,4-di-N-oxide,
3-(1,4-dioxo-2-quinoxalinemethylene)-carbazinic acid methyl ester.

8. Halogenated hydroxydiphenyl ethers:
2-hydroxy-2'4,4'-trichloro-diphenyl ether.

9. Nitrohydroxydiphenyl ethers.

10. Optionally halogenated salicyclic acid anilides.

11. Triarylmethylimidazoles:
di-(phenyl)-2-chlorophenyl-imidazolyl(1)-methane.

12. Vitamins.

13. 3-Hydroxy-2-methyl-4-pyrone.

14. 2-Mercaptoimidazole.

15. Ethoxylated alcohols:
such as $R-O(CH_2CH_2O)_nH$.

16. 2-Bromo-5-nitrothiazole.

17. Guanidines.

18. N-Substituted aminoacetic acids.

19. β-nitropropionic acid.

20. Phenylcyclopropylamine.

21. 2-(4-Thiazolyl)-benzimidazole.

22. Piperazine and its salts.

23. benzodiazepinone derivatives.

24. Dihydroxydiphenylsulphides.

25. 4,5-Dihydroxy-2,4,6-octatrienedicarboxylic acids.

26. 2-Formyl-4-chlorophenoxyacetic acids.

27. Straight-chain aliphatic alcohols.

28. 2-Chloro-10-(3-dimethylaminopropyl)-phenothiazine.

29. Acetoxybenzoic acid.

30. Auxins:
3,5-di-sec.butyl-α,β, γ-trihydroxy-1-cyclopentenevaleric acid,
3,5-di-sec. butyl-γ-hydroxy-β-oxo-1-cyclopentenevaleric acid.

Besides having a good microbicidal action, the compounds of the present invention have a good anthelmintic action. In therapeutically effective doses, they are excellently compatible, and are outstandingly effective against:
Helminths
nematodes, such as ascaridae, trichostrongylidae ancylostomatidae or strongylidae;

cestodes, such as anoplocephalidae or taenidae.

The agents containing the active substances of formula I according to the invention can be used for the control of parasitic helminths in domestic animals and productive livestock, e.g. cattle, sheep, goats, horses, pigs, cats, dogs and poultry. They can be administered to the animals both as a single dose or as repeated doses, the single doses being preferably between 25 and 1000 mg of active substance per kg of body weight depending on the species of animal. A better action is obtained in some cases by a protracted administration, or similar overall doses may suffice. The active substances or mixtures containing them can also be added to the feed or to the drinking trough. The prepared feed contains the substances of formula I preferably in a concentration of ca. 0.05 to 1 per cent by weight.

EXAMPLE 1

51.4 g of 4-chlorophenyl are dissolved in 100 ml of benzene and 31.6 g of anhydrous pyridine. While stirring, a solution of 33.8 g of glutaric acid dichloride in 100 ml of benzene is added dropwise within 30 minutes at 5–10°C. The temperature of the reaction mixture is allowed to rise to 20°C and the precipitated pyridine hydrochloride is filtered off. The benzene solution is washed with water, dried over sodium sulphate, and then completely concentrated in a water-jet vacuum. The residual glutaric acid di-(4-chlorophenyl) ester (70 g) is heated to 120°C and, with stirring, treated at this temperature within 15 minutes with 160 g of anhydrous aluminum chloride. The rapidly congealing reaction mass is heated to 160°C and then 160 ml of 1,2,4-trichlorobenzene are added. The reaction solution is stirred for 3 hours at 160°C and then poured into 3 liters of ice water. The aqueous portion is isolated and the organic portion is subjected to steam distillation. The residue is filtered off, dried in vacuo, and subsequently recrystallised from chlorobenzene to yield 43.4 g of 3-bis-(2-hydroxy-5-chlorobenzoyl)-propane with a melting point of 156°–157°C. A mixture of 29.9 g of 1,3-bis-(2-hydroxy-5-chloro-benzoyl)- propane, 50 g of hydrazine hydrate, 56 g of potassium hydroxide, and 250 ml of diethylene glycol is refluxed for 2 hours. Excess hydrazine hydrate is then distilled off and the temperature of the reaction mixture is raised to 195°C. After 2 hours the reaction mixture is stirred into 2 liters of ice water and the whole batch is acidified with concentrated hydrochloric acid. The precipitated compound of the formula III

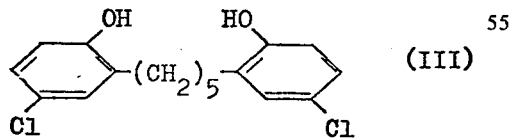

(III)

is filtered off, washed with water, and dried in vacuo. The yield is 26.8 g. Melting point: 120°C to 122°C. The compound which is purified by recrystallisation from chloroform melts at 126°C to 127°C. The yield of pure compound is 20.5 g The compounds of the formula II and IV to VII listed on pages 3 and 4 are manufactured in the same manner:

Table A

| Compound of the formula | Melting point in °C |
| --- | --- |
| II | 158 to 159 |
| IV | 147 to 148 |
| V | 135 to 136 |
| VI | 142 to 144 |
| VII | 129 to 130 |

EXAMPLE 2

It is possible to manufacture the compounds of the following Table B according to formula XV in the manner of Example 1 or of one of the methods cited hereinbefore.

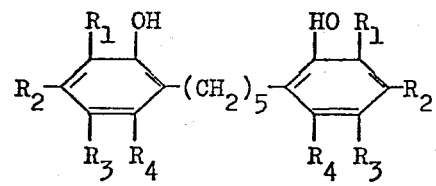

Table B

| Compound No. | $R_1$ | $R_2$ | $R_3$ | $R_4$ |
| --- | --- | --- | --- | --- |
| 1 | H | Cl | H | H |
| 2 | H | Br | H | H |
| 3 | H | Cl | Br | H |
| 4 | H | Br | Cl | H |
| 5 | H | Br | Br | H |
| 6 | H | Br | H | Br |

Determination of the minimum inhibiting concentrations (MIC) against bacteria and fungi:

Stock solutions (1.5%) of the compounds of formula I in methylcellosolve are prepared, and these are subsequently diluted so that the incorporation of 0.3 ml of each of the stock solutions and of their dilutions in 15 ml each time of warm nutrient-agar produces a concentration series of 300, 100, 30, 3, 1, etc. ppm of active substance in the agar. The mixtures are poured while still warm into dishes and, after they have solidified are inoculated with the following test organisms:

Gram-positive bacteria
*Staphylococcus aureus,*
*Sarcina ureae,*
*Streptoococcus faecalis,*
*Streptococcus agalactiae,*
*Corynebacterium diphteroides,*
*Bacillus subtilis,*
*Mycobacterium phlei.*
Gram-negative bacteria
*Escherichia coli,*
*Salmonella pullorum,*
*Salmonella cholerae-suis,*
*Bordetella bronchiseptica,*
*Pasteurella multocida,*
*Proteus vulgaris.*
*Proteus rettgeri,*
*Pseudomonas fluorescens,*
*Pseudomonas aeroginosa.*
Fungi:
*Trichophyton gypseum,*
*Trichophyton gallinae,*
*Trichophyton verrucosum,*

Candida albicans,
Candida krusci,
Aspergillus niger,
Aspergillus flavus,
Pencillium funiculosum,
Pencillium expansum,
Trichoderma viride,
Fusarium oxysporum,
Chaetonium globosum,
Alternaria tenuis,
Paecilomyces varioti,
Stachybotrys atra.

After an incubation of 48 hours at 37°C (bacteria) and 5 days at 28°C (fungi), the minimum concentration (ppm) of the active substances with which the growth of the test organisms is inhibited is determined.

Values which are clearly below the starting concentration of 300 ppm are reported for the compounds of the formula I as minimum inhibiting concentration (MIC).

Determination of the microbicidal action

A. In order to determine whether the active substances have destroyed the test germs (biocidal effect) or merely inhibited them in their growth (biostatic effect), sterile filter paper disks of 20 mm diameter are placed on the inoculation sites of the germs exhibiting no growth, and, after a contact time of 30 minutes, the germs are transferred by means of these disks to sterile agar blocked with respect to the active substances with Tween 80. The contact time is again 30 minutes. If no growth of the transferred germs on the secondary agar dish is observed, the germs have been destroyed by the active substance in the first dish, i.e. the active substance in the respective concentrations has a biocidal action on the germs examined.

The following additional test is carried out in order to confirm the preceding finding:

B. Active substances of formula I are used to prepare the following solutions:
5% of active substance,
5% of Na-N-cocos-$\beta$-aminopropionate,
20% of permutite water,
70% of ethyl cellosolve (ethylene glycol monoethyl ether).

Aliquot parts of these solutions are converted with sterile distilled water into emulsions of 100 ppm, 500 ppm, 250 ppm and 125 ppm active substance content.

Samples of 9.9 ml of the emulsions are inoculated with 0.1 ml of germ suspensions (ca. $10^7$ germs/ml).

Test organisms:
Staphylococcus aureus,
Strephylococcus faecalis,
Bacillus subtilis,
Proteus vulgaris.

After an induction period of one minute, a loop of the inoculated emulsions is placed in each case into 10 ml of sterile brain-heart-infusion-broth; after an incubation time of 24 hours at 37°, the brain-heart-infusion-broth is examined for turbidity (germ growth).

The tested compounds of formula I exhibit in the above tests a biocidal action.

EXAMPLE 3

The compounds of the formula I are dissolved in a suitable formulation (ethyl cellusolve/dimethyl formamide). The three substrates listed below are put into the bath and then squeezed out between 2 aluminum sheets. The substrates are then dried in the air. The squeezing is carried out so that there remains in case a) 1%, in b) 0.5% or in c) 0.25% of active substance on the fabric.

1. Reinforced cotton, causticised, bleached weight per m$^2$: 121 g.
2. Polyamide, nylon staple fabric, fixed, bleached, weight per m$^2$: 140 g.
3. Polyester, "Dacron" staple fabric, type 54, fixed, bleached, weight per m$^2$: 130 g.

The substrates are then tested against the following 7 test organisms according to the agar diffusion test (modified AATC test nethod 90, 1970):

Bacteria
Staphylococcus aureus ATCC 6538
Escherichia coli NCTC 8196
Proteus mirabilis NCTC 8309
Pseudomonas aeruginosa NCTC 8060
Fungi
Candida albicans ATCC 10'259
Trichophyton mentagrophytes ATCC 9533
Aspergillus niger ATCC 6275

The test plates consist of a twin layer agar, i.e. of a base layer of uninocculated nutrient agar and a surface layer of inoculated nutrient agar.

Bacteria: nutrient agar
Fungi: mycophil agar

The filtered bacillus suspension is poured on a congealed base layer and after the inoculated layer has congealed, paper discs of 20 mm diameter are placed on the treated substrates. The bacteria and candida plates are incubated for 24 hours at 37°C; the fungi plates are incubated for 3 to 4 days at 28°C. After the incubation the plates are evaluated for inhibition zones. If there are no inhibition zones, the growth beneath the test samples is examined under a magnifying glass.

The compounds of the formulae II to VII and compounds 1 to 6 exhibit in conjunction with the substrates used a good action against bacteria and fungi, for example Staphylococcus aureus, Proteus mirabilis, Candida albicans, Trichophytone mentagrophytes.

EXAMPLE 4

The substrates according to the invention are incorporated into a nutrient medium together with soap and the effectiveness is determined by the agar incorporations test.

1. Staphylococcus aureus ATCC 6538
2. Streptococcus faecalis ATCC 1041
3. Cornynebact. minutissimum NCTC 10288
4. Candida albicans ATCC 10259
5. Trichophyton mentagrophytes ATCC 9533

Nutrient medium for 1 to 3: tryptone-glucose extract agar
Nutrient medium for 4 and 5: mycophil agar.

A 0.5% solution is prepared with sterilised water from a base soap compound. Sufficient of this stock solution is given to hot, sterile, liquid agar so that the nutrient medium contains 500 ppm soap.

The test substances are dissolved in dimethyl sulphoxide, content 500 ppm. The active substance solution is put into sterilised Petri dishes in amounts of 0.2 and 0.1 ml repsectively and treated and thoroughly mixed with 10 ml of nutrient medium which contains 500 ppm of soap. (Thus 10 and 5 ppm respectively are mixed in the nutrient medium).

After the plates have congealed the bacillus suspensions are dropped thereon with a Pasteur pipette or with an inoculation device. Bacilli 1 to 4 are incubated for 24 hours at 37°C and bacillus 5 is incubated for 5 days at 28°C. In this way it is determined wheter the bacilli have grown or not. The compounds of the formulae II to VII exhibit good activity against the tested micro-organisms.

I claim:
1. Bis-hydroxyphenyl-alkanes of the formula I

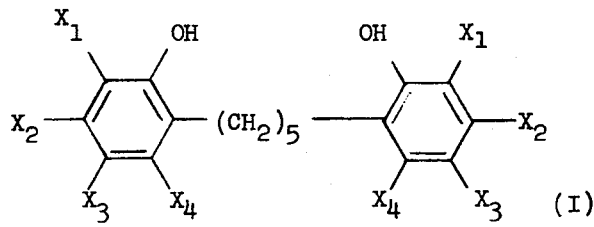

wherein one of the radicals $X_1$ to $X_4$ represents chlorine, bromine, and the others represents hydrogen, chlorine, bromine, or alkyl with 1 to 4 carbon atoms.

2. Bis-hydroxyphenyl-alkanes according to claim 1, wherein one of the radicals $X_3$ or $X_4$ represents chlorine or bromine and the other represents hydrogen, and $X_1$ and $X_2$ represent hydrogen, chlorine, bromine, or alkyl with 1 to 4 carbon atoms.

3. Bis-hydroxyphenyl-alkanes according to claim 1, wherein $X_1$ and one of the radicals $X_2$, $X_3$ and $X_4$ represents hydrogen, one of the radicals $X_2$, $X_3$ and $X_4$ represents chlorine or bromine, and the remaining radical $X_2$, $X_3$ or $X_4$ represents hydrogen, chlorine, bromine or methyl.

* * * * *